(12) United States Patent
Önell et al.

(10) Patent No.: US 8,437,963 B2
(45) Date of Patent: May 7, 2013

(54) METHOD, COMPUTER PROGRAM PRODUCT AND SYSTEM FOR ENABLING CLINICAL DECISION SUPPORT

(76) Inventors: Annica Önell, Uppsala (SE); Kerstin Wall, Uppsala (SE); Peter Forsgren, Uppsala (SE); Anita Kober, Uppsala (SE)

( * ) Notice: Subject to any disclaimer, the term of this patent is extended or adjusted under 35 U.S.C. 154(b) by 117 days.

(21) Appl. No.: 12/865,954

(22) PCT Filed: Feb. 6, 2009

(86) PCT No.: PCT/SE2009/000073
§ 371 (c)(1),
(2), (4) Date: Aug. 3, 2010

(87) PCT Pub. No.: WO2009/099379
PCT Pub. Date: Aug. 13, 2009

(65) Prior Publication Data
US 2010/0332143 A1    Dec. 30, 2010

Related U.S. Application Data

(60) Provisional application No. 61/027,048, filed on Feb. 8, 2008.

(30) Foreign Application Priority Data

Feb. 8, 2008  (SE) ...................................... 0800289

(51) Int. Cl.
*G01N 33/48*    (2006.01)
(52) U.S. Cl.
USPC ........................................................... 702/19
(58) Field of Classification Search ...................... 702/19
See application file for complete search history.

(56) References Cited

U.S. PATENT DOCUMENTS 6,306,087 B1 * 10/2001 Barnhill et al. ............... 600/300

FOREIGN PATENT DOCUMENTS

| WO | 96/12187 A1 | 4/1996 |
|---|---|---|
| WO | 2004/025251 | 3/2004 |
| WO | 2005/103300 A2 | 3/2005 |
| WO | 2006/163474 A2 | 12/2006 |
| WO | 2008/037479 A1 | 3/2008 |

OTHER PUBLICATIONS

Steele, et al., "Using Computerized Clinical Decision Support for Latent Tuberculosis Infection Screening", American Journal of Preventive Medicine, 2005, vol. 28(3), 281-283.
Evans, et al., "A Computer-Assisted Management Program for Antibiotics and Other Antiinfective Agents", The New England Journal of Medicine, 1998, 232-238.
Harpole, et al., "Automated Evidence-based Critiquing of Orders for Abdominal Radiographs: Impact on Utilization and Appropriateness", Journal of the American Medical Informatics Association, Nov./Dec. 1997, vol. 4, No. 6, 511-521.
Mendoça, "Clinical Decision Support Systems: Perspectives in Dentistry", Journal of Dental Education, Jun. 2004, 589-597.
Komata, et al., "Letters to the Editor", J Allergy Clin Immunol, May 2007, 1272-1274.
English translation of Office Action for corresponding Japanese Patent App. No. 2010-545826, drafting date Dec. 25, 2012, dispatch date Jan. 4, 2013.

* cited by examiner

*Primary Examiner* — Jerry Lin
(74) *Attorney, Agent, or Firm* — Porter, Wright, Morris & Arthur LLP

(57) ABSTRACT

A method enables clinical decision support based on test results for a plurality of tested biomarkers. The method is executed by a data reduction module (15) and comprises the steps of receiving the test results from a testing facility (11); accessing a predefined structure in which available biomarkers are associated with hosts, at least one host being associated with a plurality of biomarkers; identifying a set of hosts by mapping the tested biomarkers to the structure; assigning a host value to each host in said set of hosts based on the test results of the tested biomarker(s) mapped to the host; and providing input data indicative of the set of hosts and the assigned host values for input to a computer-based decision engine (13) for generating the clinical decision support (12). The data reduction module (15) may be included in a system and implemented by computer-executable instructions running on a data processing device, such as a PC or a web server.

20 Claims, 4 Drawing Sheets

METHOD, COMPUTER PROGRAM PRODUCT AND SYSTEM FOR ENABLING CLINICAL DECISION SUPPORT

RELATED APPLICATIONS

The present application is a 371 of PCT/SE2009/000073 filed Feb. 6, 2009 and claims priority under 35 U.S.C. §119 to U.S. Application Ser. No. 61/027,048 filed Feb. 8, 2008.

FIELD OF THE INVENTION

The present invention relates to the field of diagnosis of diseases, and in particular to diagnosis of allergy and/or autoimmune diseases using a plurality of tests for a plurality of biomarkers in a patient, typically immunoglobulin levels in blood. Specifically, the invention relates to a computerized tool for improving such diagnosis.

BACKGROUND ART

Accurate diagnosis of diseases has always been one of the fundamentals in health care. The process of making a diagnosis can take many forms, like symptom-based, patient history-based and test-based diagnosis. In test-based diagnosis, measured levels of biomarkers in body-fluids (e.g. IgE in blood is indicative of allergy, and sugar in the urine is indicative of diabetes) are used for pinpointing the disease of the patient. Furthermore, physicians tend to combine symptom-based and test-based diagnosis in order to accurately state the underlying disease.

In recent years, the availability of tests for molecular biomarkers has increased immensely. It is now common that a panel of tests is performed and the result of these, in combination with patient history, forms the basis for diagnosis. As long as the number of tests is less than around 10, this is acceptable for the average physician to handle "in his head". However, when the physician has to make decisions based on 20-100 individual test results, the risk for misinterpretation and confusion increases drastically.

In order to improve the decisions made by the physician or decrease the number of misinterpretations and errors made, clinical decision support systems (CDSSs) have been developed, designed to improve clinical decision-making related to diagnostic or therapeutic processes of care. CDSSs address activities in many fields, such as the selection of drugs (see e.g. "A computer-assisted management program for antibiotics and other antiinfective agents" by Evans et al., N Engl J. Med. 1998; 338:232-238) and the screening for latent tuberculosis infection (see e.g. "Using computerized clinical decision support for latent tuberculosis infection screening" by Steele et al., Am J Prev Med. 2005; 28(3):281-4). Furthermore, there are different support tools for interpretation of images (see e.g. "Automated evidence-based critiquing of orders for abdominal radiographs: impact on utilization and appropriateness" by Harpole et al., J Am Med Inform Assoc. 1997; 4:511-521, and US 2005/0102315).

Most CDSSs have approximately the same structure, e.g. as described in "Clinical decision support systems: perspectives in dentistry" by Mendonca in J Dent Educ. 2004 June; 68(6):589-97, which is incorporated by reference herein. In a typical CDSS, there is a working memory (often referred to as a database) containing patient data, a decision (or inference) engine which uses a categorized knowledge base (containing e.g. probabilities for disease given a test result). There may be an explanation module available, which transforms the output from the decision engine into messages with context.

One CDSS for interpretation of test results in a diagnostic situation is disclosed in WO 2005/103300, in which a statistical pattern recognition algorithm is applied to a panel of test results relating to autoimmune diseases. The algorithm compares the panel of test results with a multitude of reference data sets for previously diagnosed patients, each reference data set including values for each of a plurality of specific autoantibodies and a diagnosed disease. The algorithm applies a k-nearest neighbor process to the panel of test results and the reference data sets to produce a statistically derived decision indicating whether the panel of test results is associated with none, or one or more of the specific diseases.

WO 96/12187 discloses an automated diagnostic system capable of complex pattern recognition from multivariate laboratory data, using trained neural networks.

The prior art further comprises US 2006/0013773, which discloses a technique for correlating blood types to food allergies and food hypersensitivities.

U.S. Pat. No. 5,692,220 discloses a decision support system for hematopathology diagnosis, in which test results are input to a decision engine which compares them with patterns corresponding to specific patient conditions. The matched patterns are arranged in a hierarchy in accordance with predetermined rules.

A common problem in designing a prior art CDSS is that the complexity of its decision engine increases rapidly with the number of available test results. Clearly, this causes problems in fields where a large number of biomarker tests are available, and where new tests are constantly being developed. One such field is allergy and autoimmune diseases, in which several hundreds, if not thousands, of different biomarker tests are available.

Furthermore, it may be desirable to combine test results with demographics and observed symptoms, in order to improve the accuracy of the diagnosis provided by the decision engine and to allow the decision engine to suggest relevant follow-up tests. This will increase complexity of the decision engine even further.

SUMMARY OF THE INVENTION

It is an object of the invention to overcome or mitigate at least some of the above-identified limitations of the prior art.

This and other objects, which may appear from the description below, are at least partly achieved by means of a method for enabling clinical decision support, a computer program product and a system for enabling clinical decision support according to the independent claims, embodiments thereof being defined by the dependent claims.

According to a first aspect of the invention there is provided a method for enabling clinical decision support based on test results for a plurality of tested biomarkers, wherein each test result is given in a first resolution of values. The method comprises: receiving the test results; accessing a predefined structure in which available biomarkers are associated with hosts, at least one host being associated with a plurality of biomarkers; identifying a set of hosts by mapping the tested biomarkers to the structure; assigning a host value to each host in the set of hosts based on the test results of the tested biomarker(s) mapped to the host, wherein the host value is given in a second resolution of values; and providing input data indicative of the set of hosts and the assigned host values for input to a computer-based decision engine for generating the clinical decision support.

By proper design of the predefined structure, which is suitably designed based on clinical experience and research to represent known relationships between biomarkers and hosts, it is possible to reduce the amount of input data to the decision engine. As such, this enables the complexity of the decision engine to be reduced. Furthermore, the first aspect enables the decision engine to be designed to process hosts and host values instead of test results for individual biomarkers, to provide the desired clinical decision support. The data processing in the decision engine is suitably based on the predefined structure as well. This also has the potential of reducing the complexity of the decision engine, since the input data will inherently reflect clinical experience and research. After-developed tests for new biomarkers can easily be accommodated for, by updating the predefined structure, typically by associating the new biomarkers with one or more existing hosts and/or by adding one or more hosts.

In one embodiment, the structure comprises hosts in a hierarchy of levels. Such a structure may be used to reflect clinical experience and research, to define subtype-supertype relationships among the hosts/biomarkers. For example, different levels in the structure may represent classifications of the hosts at different degrees of detail. The use of a hierarchical structure may enable efficient processing, e.g. with respect to the mapping of the tested biomarkers. Further, the mapping of biomarkers can be done at one or more selected levels of the structure depending on the desired detail of the resulting input data.

In order to further reduce the complexity of the decision engine, the second resolution may be lower than the first resolution. This will reduce the amount of input data to the decision engine for a given set of test results.

In another embodiment, the test results or the host values are scaled based on patient-specific background data for the test results. The patient-specific background data may comprise at least one of demographic data, anamnesis, heredity factors, response pattern, patient history and genetic data. This allows for a reduced complexity of the decision engine which, for example, may be designed for an average patient.

The test results may also be scaled to match the response scale between different biomarkers. This allows the decision engine to disregard differences in response scale, thereby simplifying the design of the decision engine.

In one embodiment, the tested biomarkers are members of the Immunoglobulin super-family, and tested for in blood. For example, the tested biomarkers may be antibodies.

In one particular embodiment, the clinical decision support is related to diagnosis of allergy or autoimmune diseases.

According to a second aspect of the invention there is provided a computer program product comprising instructions for causing a computer to perform the method of the first aspect.

According to a third aspect of the invention there is provided a system for enabling clinical decision support based on test results for a plurality of tested biomarkers, wherein each test result is given in a first resolution of values. The system comprises a component for receiving said test results; a component for accessing a predefined structure in which available biomarkers are associated with hosts, at least one host being associated with a plurality of biomarkers; a component for identifying a set of hosts by mapping the tested biomarkers to the structure; a component for assigning a host value to each host in the set of hosts based on the test results of the tested biomarker(s) mapped to the host, wherein the host value is given in a second resolution of values; and a component for providing input data indicative of the set of hosts and the assigned host values for input to a computer-based decision engine for generating the clinical decision support. Each such component may be embodied as software, hardware or a combination thereof.

In one embodiment, the computer-based decision engine is included in the system.

In one embodiment, all components are integrated in a unitary device, which may be a server, a personal computer, an analytical instrument, or any other device with data processing ability.

The system may further comprise a component for scaling the test results or the host values based on patient-specific background data for the test results.

The system may further comprise a component for generating the test results. In one embodiment, this component comprises an analytical instrument specifically designed to test predefined subsets of biomarkers, preferably using an in vitro IgE ab detection technology.

The computer program product and the system according to the second and third aspects enable the same effects and advantages as the method according to the first aspect. It is also to be understood that the different embodiments described in relation to the first aspect, and the associated advantages and effects, are equally applicable to the second and third aspects.

Still other objectives, features, aspects and advantages of the present invention will appear from the following detailed description, from the attached dependent claims as well as from the drawings.

BRIEF DESCRIPTION OF THE DRAWINGS

Embodiments of the invention will now be described in more detail with reference to the accompanying schematic drawings, in which like elements are designated by the same reference numerals.

DEFINITIONS

For the purpose of the following description, and for clarity, the following definitions are made:

A patient denotes a subject that may or may not have a disease. A patient is typically a human, but may be any living organism, in particular a mammal.

A body-fluid denotes a liquid in a living organism, including (but not limited to) blood, urine, tears, saliva, lymph, semen, feaces, etc.

A biomarker is a component in a body-fluid that can be detected or quantified using an analytical instrument. Biomarkers include, but are not limited to, proteins and metabolites.

Immunoglobulin denotes a class of biomarkers, being members of the Immunoglobulin super-family. This family includes, but are not limited to, Antibodies (e.g. IgA, IgD, IgE, IgG, IgM), T cell receptor chains, Class I MHC, Class II MHC, beta-2 microglobulin, CD4, CD8, CD19, CD3-γ, -δ and -ε chains, CD79a, CD79b, CD28, CD80, CD86, Killer-cell immunoglobulin-like receptors (KIR), CD2, CD48, CD22, CD83, CTX, JAMs, BT-IgSF, CAR, VSIG, ESAM), Intercellular adhesion molecules (ICAMs), Vascular cell adhesion molecules (e.g. VCAM-1), Neural Cell Adhesion Molecule (NCAM), IL-1R-2, IL-1R-beta, CD121b antigen, PDGFR, IL-6R-alpha, CD126 antigen, CSF-1-R, CD115 antigen, SCFR, c-kit, CD117 antigen, FGFR-1, CEK1, PIGR, CD147, CD90, CD7, Butyrophilins, and many more.

Allergy denotes an acquired, abnormal sensitivity to a foreign substance causing allergic symptoms.

An allergen denotes an entity capable of causing allergy.

A test denotes the measurement of patient response to a particular allergen.

A host denotes the object/organism carrying or being associated with one or more particular allergen(s).

A class of hosts denotes a group or family of hosts.

DETAILED DESCRIPTION OF EMBODIMENTS OF THE INVENTION

Figure 1:
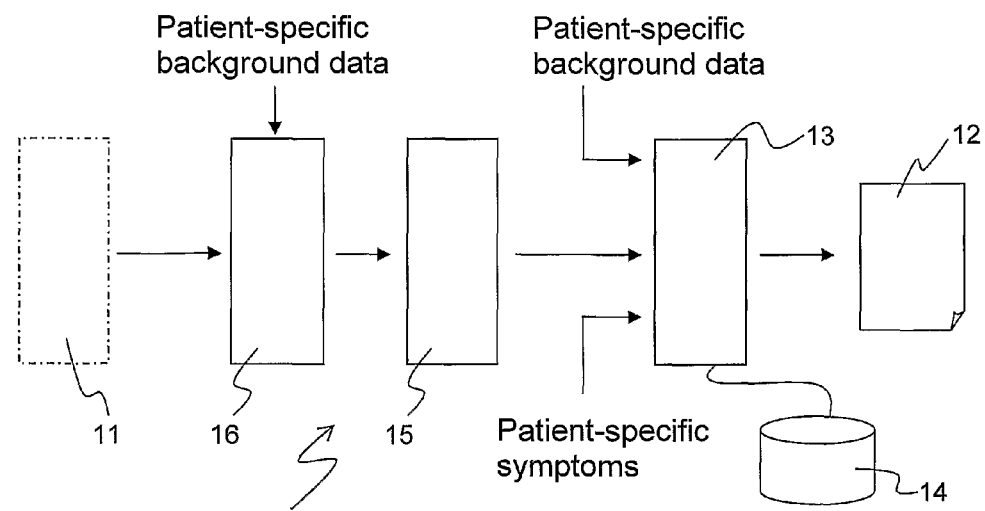
FIG. 1 is a block diagram of a system for clinical diagnosis support including an embodiment of the invention.

FIG. 1 is a block diagram of a data processing system 10 in which an embodiment of the present invention is used. The system 10 receives test data from a testing facility 11, which includes an analytical instrument for measuring a quantity of a number of biomarkers in a body-fluid, typically blood, for a patient. The measurement may be performed in vivo or in vitro. The resulting test data, i.e. a measurement value (test result) for each tested biomarker, is typically given with a high resolution within a measurement range. For example, the number of measurement steps within the measurement range may be at least 10, typically about 50-100 or more. The test data may involve any number of test results, typically more than about 10.

The system 10 receives and processes the test data, together with further patient-related data, to finally generate a patient-specific diagnosis report 12 which may aid a physician to accurately diagnose the patient. The diagnosis report 12 may, e.g., include a suggested diagnosis, and a suggestion for relevant follow-up tests, as well as a full or reduced listing of the test results.

In the illustrated embodiment, the system 10 includes a decision or inference engine 13 which operates, i.a., on preprocessed test data to generate the diagnosis report. The decision engine 13 may be configured according to conventional technology to use a knowledge base 14 which stores relevant knowledge in computer-readable form. The decision engine 13 may include a set of rules derived from experts and evidence-based medicine in relation to a set of available biomarkers. The set of rules may thus define the patient-specific comments, derived from the knowledge base 14, to appear on the report 12 based on the input data.

The input data to the decision engine 13 may also comprise patient-specific symptom data, indicating one or more symptoms observed on the patient by a physician.

The input data to the decision engine 13 may also comprise patient-specific background data, such as demographic data (age, race, domicile, etc), anamnesis, heredity factors, response pattern, genetic data, etc.

In one embodiment, the decision engine 13 is based on a ripple-down rules technology. Such a decision engine may be implemented using commercially available software, such as LabWizard®, available from Pacific Knowledge Systems.

Conventionally, it may be quite complicated to develop a decision engine that can handle a large amount of different test results and symptoms for a patient. For example, if tests are available for 100 different biomarkers, and each test result can assume any integer value in the range of 0-100, and there are 7 different symptoms to be handled, a conventional decision engine would need to include rules for $101^{100} * 2^7 = 3.5 * 10^{202}$ different combinations.

Figure 2:
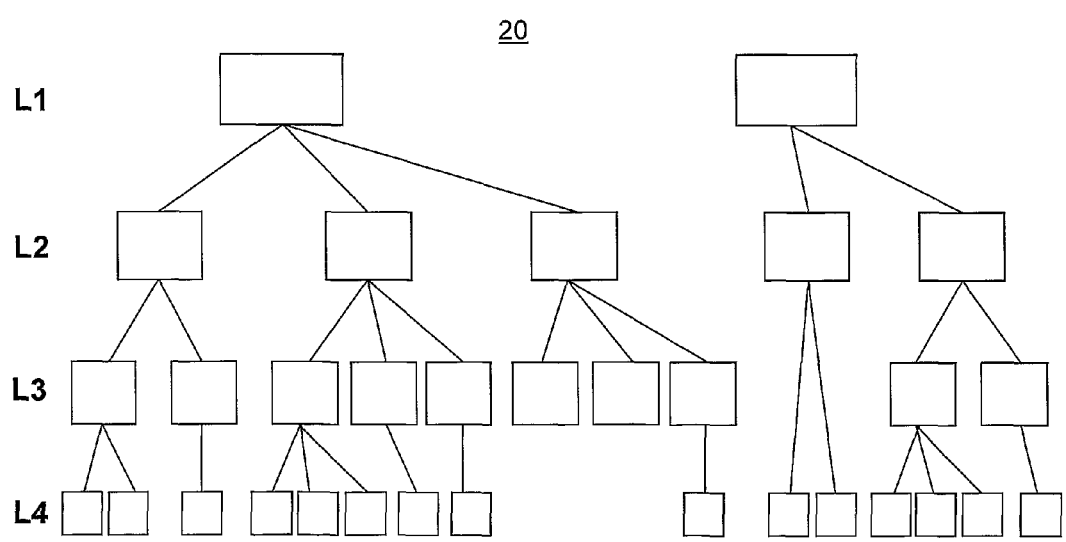
FIG. 2 shows an example of a hierarchical structure of hosts.

In order to reduce the complexity of the decision engine for a given number of test results, the system of FIG. 1 includes a data reduction module 15. The module 15 is configured to reduce the amount of data to be processed by the decision engine 13. To this end, the module 15 utilizes a structure in which the available biomarkers, i.e. the biomarkers handled by the decision engine 13, are assigned to different hosts. Each host includes or represents one or more biomarkers. A general example of such a structure 20 is shown in FIG. 2, in which the hosts are organized in a number of levels L1-L4. The structure 20 represents known relationships between biomarkers and hosts, and is set up based on clinical experience and research.

The module 15 maps the tested biomarkers to the hosts defined by the predefined structure 20, and thus identifies a set of hosts, in which each host includes one or more of the tested biomarkers. The module 15 also assigns a value to each such host, based on the test result(s) of the biomarker(s) included in the host. This value may be given by any suitable statistical function operating on the test results for a host, such a maximum, median, arithmetic mean, geometric mean, harmonic mean, etc.

The set of hosts, and the assigned values, are supplied as input data to the decision engine 13. The input data may be presented to the decision engine in any suitable format, e.g. as text, or as numbers in any base (binary, hexadecimal, etc), or combinations thereof.

For example, for biomarkers indicating presence of specific allergens, the host may denote a class of objects/organisms carrying one or more specific allergens. In one example, the predefined structure divides the available biomarkers into five different main groups or hosts: "Food", "Pollen", "Mite", "Mould" and "Animals". As indicated in FIG. 2, the structure 20 may be organized in a hierarchy of hosts on different levels L1-L4. The above-mentioned main groups may be organized on the root level L1, and have subgroups (hosts) in one or more sublevels L2-L4. In one example, the main group "Pollen" may have the subgroups (on level L2) "Trees", "Grass" and "Herbs", and the subgroup "Trees" may have the subgroups (on level L3) "Oak", "Birch" and "Elm", etc. Irrespective of the number of subgroups, the complexity of the decision engine is governed by the number of main groups. It should be realized that the complexity of the decision engine is reduced significantly.

There are several conceivable variants for the data reduction module's selection of hosts to be included in the input data for the decision engine. In one variant, all hosts in the predefined structure 20 that can be mapped to the tested biomarkers may be included in the input data. For example, if a biomarker for birch has been tested, the module may include the hosts "Birch", "Trees" and "Pollen" in the input data.

In another variant, the data reduction module may include a set of predetermined rules that control the selection of hosts based on the test values and/or biomarkers included in the test data. For example, if the test data includes test results (optionally with the additional condition that these test results are significant) for more than three different tree pollens, these test results may be grouped into a host for deciduous trees. If the test data only includes test results for pollen relevant to birch trees, these test results may be grouped into a host for birch. In another example, all test results relating to mite are by default grouped into the corresponding main host. If the number of the results is very large, the rules may stipulate that all test results should be grouped into the main hosts, or at least hosts on level L1 or L2.

In yet another variant, the selection of hosts is controlled by an input parameter to the data reduction module. For example, the input parameter may indicate the qualification level of the person to interpret the diagnosis report. If this person is a specialist, it is acceptable/desirable for the diagnosis report to include much detail about the suggested diagnosis and the test results, and thus the input data should include hosts on the lower levels of the structure 20 (cf. L3 and L4). If the person is a general practitioner, the diagnosis report should be simple and straight-forward, and the input data should primarily be based on hosts from the higher levels of the structure 20 (cf. L1 and L2)

The data reduction module 15 can be used to reduce the apparent number of input variables to the decision engine 13. This feature may be exploited to reduce the complexity of the decision engine 13 and/or to allow for other information than test results to be used as input variables to the decision engine 13 without unduly increasing its complexity. As indicated in FIG. 1, patient-specific symptom data can be used as such an input variable. For example, the decision engine may be configured to handle a given set of symptoms, with a value of either 0 or 1, indicating absence and presence of the symptom, respectively. Similarly, patient-specific background data (anamnesis, demographics, etc) may be used as one or more input variable(s) to the decision engine.

It should be understood that the decision engine 13 should be designed to provide diagnosis support based on the input data provided by the data reduction module 15, i.e. hosts and host values. To this end, the decision engine 13 may include a set of rules which is based on a similar predefined structure as used by the data reduction module 15.

As noted above, this predefined structure represents known relationships between biomarkers and hosts, based on clinical experience and research. Thus, even though the decision engine operates on a sparse array of input data, it is constructed to provide accurate diagnosis based on clinical experience. For example, knowledge about cross-reactivity, demographics of allergy and age-dependency makes it possible to reliably predict high risk for a specific allergy of a patient for which the specific IgE of the relevant allergen was not tested for in the panel of allergen tests. It should thus be realized that since the decision engine is able to provide accurate diagnosis guidelines based on a few input variables, the above-described system allows for the use of sparse biomarker panels.

Furthermore, the reduction of input data into hosts and host values also makes it possible to condense the output of the decision engine into short and concise readable messages.

To further reduce the amount of input data to be processed by the decision engine 13, the module 15 may be configured to reduce the resolution of the assigned host values compared to the resolution of the test values. This may be achieved by quantization, either of the test values before the above-mentioned mapping, or of the values assigned to set of hosts. The quantization of a value may involve assigning the value to one of a number of value groups. For example, test values may be assigned to one of the following value groups: Undetectable, Very Low, Low, Moderate, High, Very High. These value groups may, e.g., be represented by a value 0-5.

Thus, we end of with 5 hosts that can take an integer value 0-5. With 7 different symptoms, we end up with $6^5 * 2^7 = 995000$ different combinations to be handled by the decision engine, which is significantly less than $3.5*10^{202}$ different combinations to be handled on unprocessed test results.

Returning to FIG. 1, the illustrated embodiment also includes a scaling module 16 for effecting selective context-based scaling of the test results. The module 16 may be implemented to adjust the test results based on the patient-specific background data. This allows the decision engine 13 to be based on rules for an average population, thereby simplifying the design of the decision engine. For example, when testing children, the response scale may be different to adults. Thus, the module may be configured to scale (typically increase) the test results for at least certain biomarkers.

Figure 3:
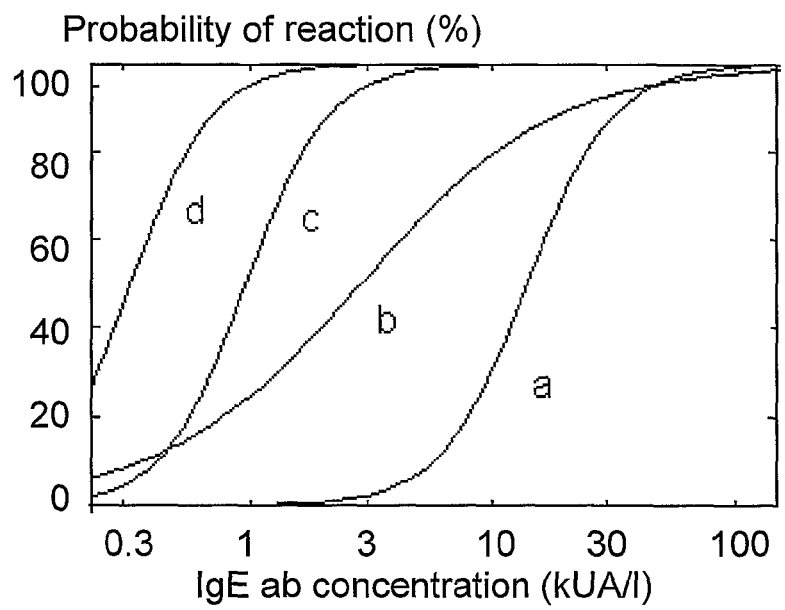
FIG. 3 is a graph relating the probability for allergic reaction to IgE biomarker values for different food allergens.

Additionally or alternatively, the module 16 may be configured to rescale the test results so as to match the response scale between different biomarkers. For example, different allergens may have different cut-off levels, depending partly on the inherent allergenicity of the respective allergen. Thus, a low test value for one biomarker may result in a higher probability for allergy than a high test value for another biomarker. This is valid even if the biomarkers are very similar, such as IgE-antibodies directed towards a variety of allergens. As shown in FIG. 3, the probability of low values (~1 kUA/l) of the IgE biomarker for allergens c and d is higher than the probability of high values (~10 MA of the IgE biomarker for allergen a. The context-based scaling may account for this, by scaling one or more of the test values to match the probabilities of reaction. This allows the decision engine to disregard differences in response scale, thereby simplifying the design of the decision engine.

In an alternative embodiment (not shown), the scaling module 16 is arranged downstream the data reduction module 15 to operate on the values assigned to the set of hosts, instead of the test values from the testing facility. In yet another embodiment, all or part of the scaling functionality may be incorporated in the decision engine 13.

Figure 4:
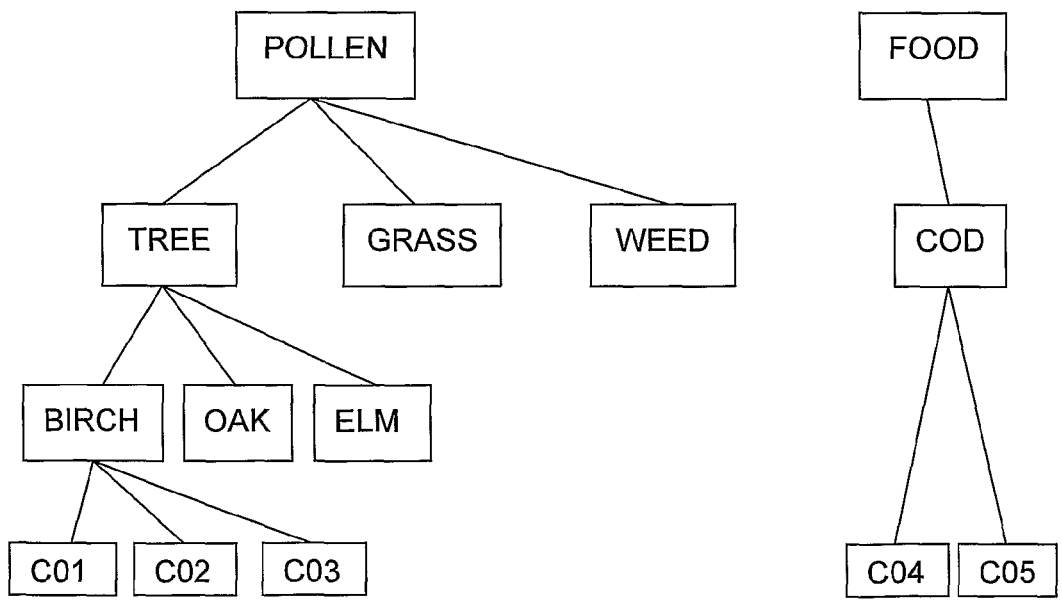
FIG. 4 shows a part of a predefined structure for top level hosts "Pollen" and "Food" according to an embodiment of the invention.

In the following, the operation of the decision engine and its use of rules will be further exemplified. Examples 1-6 are given with reference to FIG. 4, which illustrates a small part of a predefined structure for the main hosts "Pollen" and "Food". It is to be noted that the following examples are simplified for ease of understanding. In the examples, variables and values are indicated in italics.

Example 1

Symptom: Eczema

Host value: Birch in range Low

Rule: IF (Symptom=Eczema) AND (ANY Pollen>Undetectable) ⇒ Interpretation comment: "The Eczema is probably not due to Pollen"

Example 2

Symptom: Asthma

Host value: Birch in range High

Rule: IF (Symptom=Asthma) AND (ANY Pollen in ranges High TO Very High) ⇒ Interpretation comment: "The IgE antibodies detected for Birch are likely to be associated with the symptoms of Asthma"

Example 3

Symptom: Asthma
Host values: Birch in range High, Oak in range Moderate, and Elm in range Low
Rule: IF (Symptom=Asthma) AND (ANY Pollen in ranges High TO Very High) ⇒ Interpretation comment: "The IgE antibodies detected for Tree Pollen are likely to be associated with the symptoms of Asthma"

Example 4

Symptom: Eczema
Host value: Cod in range Very High
Rule: IF (Symptom=Eczema) AND (ANY Food in range Very High) ⇒ Interpretation comment: "The Eczema is likely due to Cod"

Example 5

Symptom: Eczema
Host values: Cod in range Moderate
Rule: IF (Symptom=Eczema) AND (ANY Food in range Moderate) ⇒ Interpretation comment: "The Eczema may be due to Cod"

Example 6

Symptom: Eczema
Host value: Cod in range Very Low
Rule: IF (Symptom=Eczema) AND (ANY Food in range Very Low) ⇒ Interpretation comment: "The very low IgE level to Cod is probably not associated with the Eczema"

Example 7

A patient with symptoms of asthma and eczema is tested in vitro for IgE antibodies. The following test results are obtained:
   Cat=51 kU/l
   Mugwort=23 kU/l
   Birch=3 kU/l
   Dog=2.7 kU/l
   Ragweed=0.7 kU/l
   Timothy=0.6 kU/l
   Horse=0.45 kU/l
   Rabbit=0.41 kU/l
   Mite_d1=0.57 kU/l
In this simplified example, the data reduction module is configured to assign the test results to the following pre-defined main hosts: "Pollen", "Food", "Animal", "Mite" and "Mould". Each main host is assigned a host value given by the maximum test value assigned to the host. Furthermore, the data reduction module is configured to group the host values according to the following pre-defined IgE ranges (given in kU/l): Undetectable: <0.1, Very Low: [0.1-0.5], Low: [0.5-2], Moderate: [2-15], High: [15-50], and Very High: >50.
After pre-processing in the data reduction module, the following input data for the decision engine is obtained:
   Animal=Very High
   Pollen=High
   Mite=Low
The pre-processed data is sent to the decision engine, which generates interpretation comments according to the following set of rules:

Rule: IF (Symptom=Asthma OR Rhinitis) AND (Animal in range Very High) ⇒ Interpretation comment: "The observed IgE abs to Animal is highly likely associated with the Asthma symptoms."
Rule: IF (Symptom=Asthma OR Rhinitis) AND (Pollen in range High) ⇒ Interpretation comment: "The observed IgE abs to Pollen is likely associated with the Asthma symptoms."
Rule: IF (Symptom=Asthma OR Rhinitis) AND (Mite in range Low) ⇒ Interpretation comment: "The observed IgE abs to Mite may contribute to the Asthma symptoms."
Rule: IF (Symptom=Eczema) AND (Pollen in ANY range) ⇒ Interpretation comment: "The observed IgE abs to Pollen is unlikely to be associated with the reported Eczema."
Rule: IF (Symptom=Eczema) AND ((Mite OR Animal) in ANY range>Low) ⇒ Interpretation comment: "IgE mediated allergic skin symptoms is usually related to food allergens, but direct skin contact with or inhalation of air borne allergens can occasionally contribute to skin symptoms."

One general rule of interpretation of IgE biomarker values is that the higher the values, the greater the risk of IgE mediated allergic symptoms. There are however many exceptions to the general rule, and these exceptions may be incorporated in the rules of the decision engine or in the context-based scaling. The following two examples illustrate how these exceptions can be incorporated in the context-based scaling.

Example 8

Two patients A and B have IgE responses in the Low range to egg, one patient being 1 year old and the other 30 years old. The scaling module is configured to increase, for children<6 years of age, a test result for egg in the Low range to the Moderate range. The correspondingly processed test results are sent as input data to the decision engine, which generates interpretation comments according to the following set of rules:
Rule: IF (Symptom=Eczema) AND (Egg in range Moderate) ⇒ Interpretation comment for Patient A: "The Eczema is probably due to Egg."
Rule: IF (Symptom=Eczema) AND (Egg in range Low) ⇒ Interpretation comment for Patient B: "The Eczema may be due to Egg."

Example 9

The significance of the test result for a specific allergen may be up- or downgraded regardless of age. Based on clinical experience, the scaling module may for example be configured to always downgrade test results in the Low range for wheat or soy (e.g. 1.8 kU/l) to the Very Low range. The correspondingly processed test results are input to the decision engine, which generates interpretation comments according to the following set of rules:
Rule: IF (Symptom=Eczema) AND ((Wheat OR Soy) in range Very Low) ⇒ Interpretation comment: "For Wheat/Soy, symptoms of Eczema due to these IgE antibody levels are uncommon."
Rule: IF (Symptom=Eczema) AND ((Wheat OR Soy) in range Low) ⇒ Interpretation comment: "The Eczema may be due to Wheat/Soy."

Examples 8 and 9 indicate that logic may be moved from the decision engine to the scaling module, allowing the complexity of the former to be reduced. Furthermore, the provision of the scaling module allows scaling parameters to be changed independently of the decision engine, e.g. to accommodate for new findings relating to the allergenicity of a certain biomarker.

Table 1 below is an example of a diagnosis report generated by a decision engine, based on a different set of test results. In this example, the diagnosis report includes observed symptoms, in this example rhinitis. It also includes the test results that fall in each of the above-mentioned ranges. In this example, one test result for mite falls in the range High, and one test result for grass pollen falls in the range Moderate, whereas all other test results are Undetectable. In this example, the decision engine was not only provided with the pre-processed input data, but also with the original test results. However, the diagnosis report was generated based on the pre-processed input data; the test results were in this example used for presentation purposes only.

TABLE 1

Example of a diagnosis report which is generated based on test results that are processed according to an embodiment of the invention

| | |
|---|---|
| Symptoms | {rhinitis} |
| VeryHighAllergens | |
| HighAllergens | {mite_d1 (34.7278)} |
| ModerateAllergens | {grassmix_3 (7.2496)} |
| LowAllergens | |
| VeryLowAllergens | |
| UndetectableAllergens | {dog (0.1155), cat (0.1127), weedmix_3 (0.0899), mouldmix_1 (0.1123)} |

SUMMARY

The rhinitis symptoms are likely due to mite. The IgE abs to grassmix_3 probably also contribute.
TO CONSIDER:

Possible asthma development should be investigated and monitored.
MITES

Minimizing the mite exposure can be beneficial for this patient. The observed high IgE abs level to mite is likely associated with the symptoms of rhinitis.
POLLENS The observed IgE abs to grassmix_3 are likely associated with the symptoms of rhinitis if present during pollen season. Symptoms to allergens other than pollen may get worse during the pollen season due to the additive allergen load effect.
CLOSELY RELATED ALLERGENS to grass pollen are peanut, soybean, tomato, melon, wheat, oat, barley and rye. to mite are shrimps, snails, oyster and other mite species.
DID YOU KNOW IgE mediated rhinitis usually occur seasonally for pollen, perennially for indoor inhalant allergens and at the work place for occupational allergens.
IgE mediated allergy, especially to inhalation allergens, it a strong predisposing factor for asthma development in patients with rhinitis.

The actual diagnosis report in Table 1 was generated based on the above-mentioned rules. In the illustrated example, the diagnosis report includes a SUMMARY of the diagnosis, a section TO CONSIDER, giving further advice to the practitioner, a MITES section and a POLLENS section, discussing the relevance of the significant test results to the observed symptoms, one section providing information of CLOSELY RELATED ALLERGENS, and one section providing basic information (DID YOU KNOW).

The inclusion of different sections in the diagnosis report, and the content of each section, is controlled by the aforesaid set of rules, based on the input data. For example, under POLLENS, the comment is associated with a rule "The observed IgE abs to {ModeratePollen as names} are likely associated with the symptoms of {PollenSymptoms} if present during pollen season". The variable {ModeratePollen as names} is substituted by all pollen allergens, or hosts on a suitable level in the predefined structure, that fall within the range Moderate, and the variable {PollenSymtoms} is substituted by all observed symptoms that are relevant to pollen allergy, such as rhinitis, asthma and wheeze.

It may be important that the diagnosis report is generated with an adequate complexity, i.e. that the number of comments is kept to a reasonable amount. Basically, the complexity of the report depends on the level of detail provided by the input data, e.g. the number of hosts on different levels indicated by the input data.

As mentioned above, the data reduction module may contain logic for selecting an appropriate detail for the input data. Alternatively, or additionally, similar logic may be incorporated in the decision engine, which thereby is controlled to select a subset of the hosts included in the input data to be used for generating the diagnosis report. In one variant, further explained above in relation to the data reduction module, the selection of hosts may be based on the hosts and/or host values included in the input data. In another variant, also explained above in relation to the data reduction module, the selection is controlled by an input parameter to the decision engine, e.g. indicating the qualification level of the person to interpret the diagnosis report.

Figure 5:
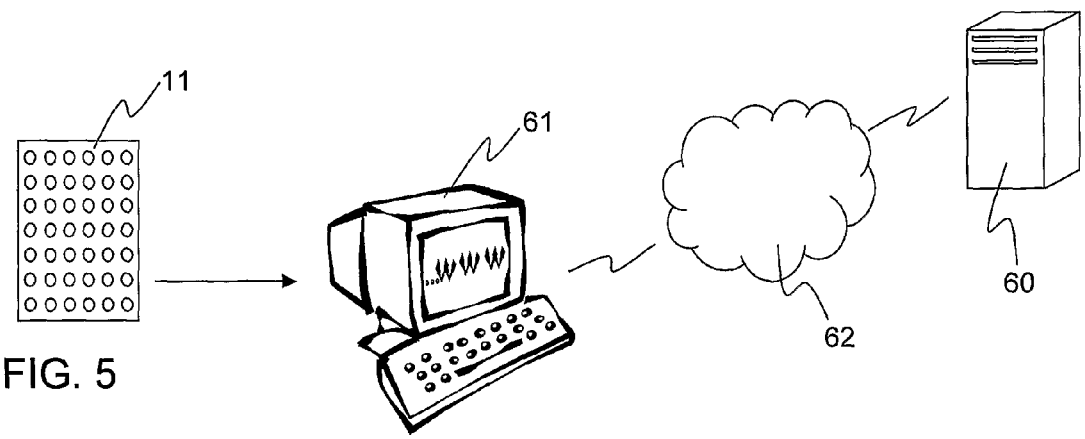
FIG. 5 is schematic view of an implementation environment for an embodiment of the present invention.

The above-described clinical decision support system can be implemented in many different environments. Preferably, the scaling module, the data reduction module and the decision engine are implemented by software run on an electronic data processing device, such as a computer. For example, as schematically shown in FIG. 5, the system may be implemented on one or more network-connected servers 60. A user may enter test data, originating from the testing facility 11, into the system via a web interface on a PC 61 connected to a public or private communication network 62 (e.g. the Internet). The resulting diagnosis reports may be provided for display to the user via the web interface, and/or they may be printed on a nearby digital printer. Alternatively (not shown), the test data may be automatically entered into the system from the testing facility 11, either via the PC 61 or via a network-interface integrated in the testing facility. In yet another alternative, the scaling module 16 and/or the data reduction module 15 may be located on the PC 61 or the testing facility 11, to provide appropriate input data to the decision engine 13 on the server 60. In still another alternative, the entire system resides locally on the PC 61 or the testing facility 11.

Figure 6:
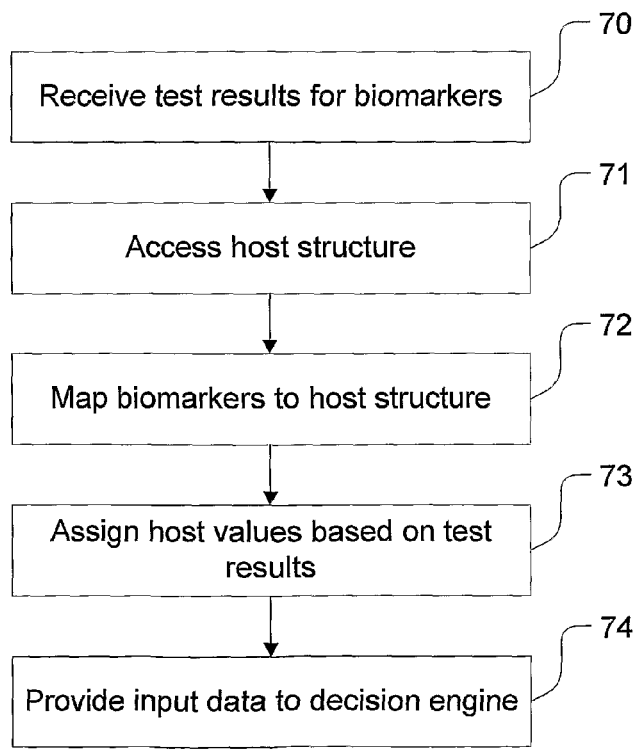
FIG. 6 is a flow chart of a method for enabling clinical decision support according to an embodiment of the invention

FIG. 6 is a flowchart to illustrate an embodiment of a method executed in a clinical decision support system, such as the system in FIG. 1, or in the PC/web server/testing facility in FIG. 5. First, test results for a plurality of tested biomarkers are received by the system (step 70). Then, a predefined host structure (c.f. structure 20 in FIG. 2) is accessed (step 71), whereupon a set of hosts are identified by mapping the tested biomarkers to the structure (step 72). The mapping identifies hosts that include or are associated with one or more of the tested biomarkers. As noted above, the set of hosts need not include all hosts that include one or more of the tested biomarkers, but could instead consist of a subset of such hosts. Then, each host in the identified set of hosts is assigned a host value based on the test results of the tested biomarkers that are mapped to the host (step 73). Finally, data indicative of the set of hosts and the assigned host values is provided for input to a computer-based decision engine for generating clinical decision support (step 74).

Figure 7:
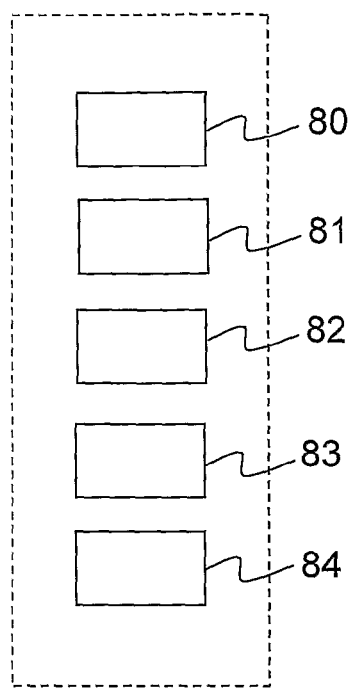
FIG. 7 is a block diagram of an exemplifying system for implementing the method in FIG. 6.

FIG. 7 is a schematic block diagram of a system configured to execute the method of FIG. 6. In the illustrated example, the system includes a component (or means) 80 for receiving the above-mentioned test results, a component (or means) 81 for accessing the host structure, a component (or means) 82 for identifying a set of hosts by mapping, a component (or means) 83 for assigning a host value to each host in the identified set of hosts, and a component (or means) 84 for providing the resulting data as input to the decision engine. As noted above, the components (means) 80-84 that define the system in this example may be implemented by special-purpose software (or firmware) run on one or more general-purpose or special-purpose computing devices. Such a computing device may include one or more processing units, e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). In this context, it is to be understood that each "component" or "means" of such an apparatus refers to a conceptual equivalent of a method step; there is not always a one-to-one correspondence between components/means and particular pieces of hardware or software routines. One piece of hardware sometimes comprises different components/means. For example, the processing unit may serve as one component/means when executing one instruction, but serve as another component/means when executing another instruction. In addition, one component/means may be implemented by one instruction in some cases, but by a plurality of instructions in some other cases. The computing device may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The computing device may include one or more communication interfaces, such as a serial interface, a parallel interface, a USB interface, a wireless interface, a network adapter, etc. One or more I/O devices may be connected to the computing device, via a communication interface, including e.g. a keyboard, a mouse, a touch screen, a display, a printer, a disk drive, etc. The special-purpose software may be provided to the computing device on any suitable computer-readable medium, including a record medium, a read-only memory, or an electrical carrier signal.

Another aspect of the invention is the possibility to use the knowledge of the hierarchical structure of biomarker and host patterns to construct efficient and cost-effective analytical instruments. Instead of such an instrument being capable of measuring a very large number of different biomarkers, it could instead be capable of measuring only the defined subsets of biomarkers required for accurate diagnosis. Furthermore, the analytical instrument could also be hiding the concept of the hierarchical biomarker and host patterns with defined subsets representing hierarchically higher hosts, optionally in combination with context-based scaling, from the operator, thereby minimizing the need for training of said operator. Such an analytical instrument would be less complex to design, simpler to operate, and therefore less costly for the end user.

This means that given a set of tests (that may be incomplete) from a patient (that may not be an "average" patient), precise diagnosis is possible using the structure of any common CDSS. It is also possible to suggest cost-effective follow-up studies by finding the complementing tests that would significantly improve the diagnosis given an incomplete set of tests from a patient.

Further Motivation of Underlying Concepts

The above-described embodiments of the present invention rely on the provision of a structure that represents known relationships between biomarkers and hosts, and typically a hierarchical structure of such hosts. Below follows a discussion to motivate the provision of such a structure.

Using the disease Allergy as a non-limiting example, it is possible to test a patient for response to allergens. A host can have several different allergens associated with it. Furthermore, the same allergen can be found in different hosts. Thus, as hypothetically exemplified in Table 2 below, it would be possible to associate the host Cat (1111) with a number of Cat-specific allergens (1001, 1002) and a number of Fur allergens (1011, 1012, 1015). Likewise, a Dog (1112) could hypothetically be associated with a number of Dog-specific allergens (1021, 1022), and a number of Fur allergens (1011, 1013), some of which may be shared (1011) with Cat. For the host Horse (1113), the individual allergenic components could be unknown. Therefore, Horse is represented by an extract containing a plurality of unknown components, said extract being known to accurately cover the majority of possible Horse allergens. Horse, Cat and Dog together form the family Mammals with fur (1100). In summary, the example in Table 2 represents a predefined hierarchical structure which is based on known relationships of allergens and their hosts.

TABLE 2

Example of a predefined hierarchical structure which is based on known relationships between allergens and their hosts 1001: Cat component 01
1002: Cat component 02
...
1011: Fur component 01     1111: Cat
1012: Fur component 02
1015: Fur component 05

1021: Dog component 01
1022: Dog component 02                    1100: Mammals
...                        1112: Dog      with fur
1011: Fur component 01
1013: Fur component 03

1031: Horse extract ——— 1113: Horse

It would be impractical to require tests for all individual allergens for all patients, due to costs and test availability. Therefore, for each host and each family there may exist defined subsets of tests that may represent the host or family. For example, if one Cat specific allergen (any of 1001, 1002) and one of the Fur allergens present in the host Cat (any of 1011, 1012, 1015) have been tested for, these two test results could be used to represent the host Cat even though several allergens were not tested. Several such defined subsets of biomarkers capable of accurately representing a host may be known. In the same fashion, Mammals with fur (1100) could be represented by at least two of the family members (i.e. any two of Cat (1111), Dog (1112) and Horse (1113)). The concept of defined subsets is therefore equally valid for hosts that in concert may represent a hierarchically higher host.

The following construction rules apply to the allergen-host structure shown in Table 2:

A host has one or more associated allergens
An allergen can be found in different hosts
Allergy to a host can be represented by tests for defined subsets of allergens associated with the host
Allergy to a class of hosts can be represented by allergy to defined subsets of the hosts included in the class of hosts

TABLE 3

Correlation coefficient between IgE biomarker values for wheat and a range of other IgE biomarker values, for two groups of subjects

| Allergen name | Spearman correlation to Wheat | |
| --- | --- | --- |
| | Group A | Group B |
| Wheat | 1 | 1 |
| Rye | 0.95 | 0.78 |
| Barley | 0.93 | 0.47 |
| Oat | 0.89 | 0.36 |
| Rice | 0.86 | 0.17 |
| Maize | 0.85 | 0.52 |
| Onion | 0.84 | 0.05 |
| Garlic | 0.84 | 0.13 |
| Orange | 0.80 | 0.11 |
| Potato | 0.79 | 0.16 |
| Buckwheat | 0.79 | 0.08 |
| Strawberry | 0.78 | 0.33 |
| Soya bean | 0.78 | 0.21 |
| Tomato | 0.77 | 0.29 |
| Sesame | 0.75 | −0.02 |
| White bean | 0.74 | 0.10 |
| Coconut | 0.71 | 0.04 |
| Carrot | 0.71 | 0.35 |
| Peanut | 0.68 | 0.17 |
| Pea | 0.67 | −0.08 |
| Almond | 0.63 | −0.09 |

One piece of evidence that such a hierarchical organization of biomarkers exists can be obtained by looking at contents of allergy databases. Table 3 above shows the correlation between wheat and a range of IgE biomarkers for foods of plant origin, for two groups of subjects. Group A consists of subjects that have confirmed elevated IgE values to wheat and grass pollen. Group B consists of subjects that have confirmed elevated IgE values to wheat but not to grass pollen. As seen in Table 3, for both group A and group B, high values of IgE for wheat result in a high probability of a high value of IgE for rye. For group A only, high IgE value of wheat correlates with the IgE values of a number of common allergens, including onion, rice and orange. This means that the detection of IgE biomarker values for wheat and grass pollen gives a detailed indication of other possible allergies: In case of elevated wheat value only, there is an indication of elevated rye values. In case of both wheat and grass pollen values being elevated, a range of indications of elevated IgE values are given, as listed in Table 3. This type of a priori information gives a basis for the hierarchical structure.

The above-described embodiments of the present invention also rely on context-based scaling of test results or host values. Below follows an exemplifying discussion on a context-based scaling function for the probability of reacting to milk at a given test result and age. The person skilled in the field of allergy and auto-immunity immediately realizes that the following discussion is generally applicable to other types of allergies, and other types of patient-specific background data.

It is previously known how the biomarker "milk allergen specific IgE antibody" is related to milk allergy as described in "The predictive relationship of food-specific serum IgE concentrations to challenge outcomes for egg and milk varies by patient age" by Komata et al., J. Allergy Clin. Immunol. 2007 May; 119(5): 1272-4 (which is incorporated by reference herein). An illustration of the relationship is provided in FIG. 8. By using this information to scale the test result (in this case the IgE antibody concentration) based on age, the decision engine would not need to handle the property age and could therefore be made simpler.

Figure 8:
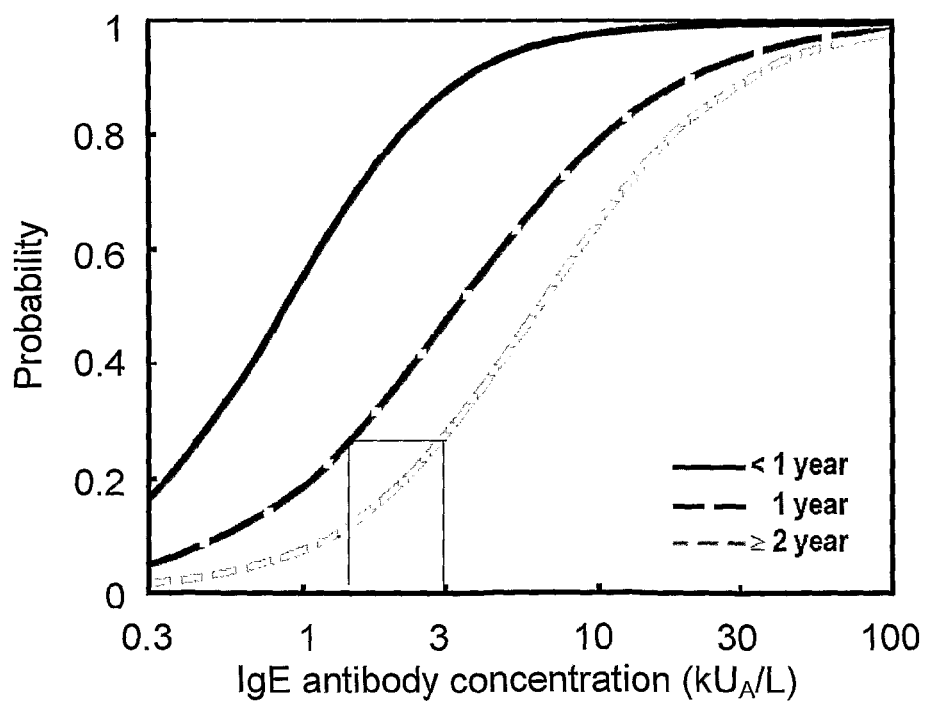
FIG. 8 is a graph relating the probability for allergic reaction to milk allergen specific IgE antibody values for different ages of patients.

In practice, the information in FIG. 8 would be utilized as follows: If a one year old child is tested for milk allergen specific IgE antibodies, and the test result is 1.3 $kU_A/L$, the test result would be scaled, based on age and the probability curve in FIG. 8, into the value that represents the same probability of developing allergy towards milk for older children. This scaling procedure is indicated in FIG. 8 as a thin line. In this particular case, the one year old child has a probability of 0.25 to be allergic to milk. For older patients, this probability is obtained for a test result of 3 $kU_A/L$. Therefore, the one year old child test result of 1.3 $kU_A/L$ is converted to 3 $kU_A/L$. In this way, one interpretation will be valid irrespective of the age of the child. In the aforesaid report by Komata et al., only children were investigated, but it is understood that the same mapping can be performed for any groups of patient ages, including adults and elderly.

The invention has mainly been described above with reference to a few embodiments. However, as is readily appreciated by a person skilled in the art, other embodiments than the ones disclosed above are equally possible within the scope and spirit of the invention, which is defined and limited only by the appended patent claims.

The present invention is applicable to diagnosis of diseases other than allergy. Basically, it is generally applicable in any diagnostics area where a number of biomarkers (for example a micro-array panel of biomarkers) are used which are correlated or related to one another and thus can be grouped into groups and subgroups, and optionally where the significance to clinical symptoms needs to be scaled in a context. Examples on alternative diagnostics areas include autoimmunity, cancer, and CNS (central nervous system) related diseases. Since the biomarkers can be grouped into groups/subgroups, a predefined structure can be formed in which hosts are associated with biomarkers, at least in a figurative sense. Thus, the skilled person can readily apply the foregoing description to alternative diagnostics areas.

In the examples above, all test results are given in a common measurement range. This is not necessary. Instead, different measurement ranges can be used for different test results. Similarly, different measurement ranges can be used for the host values assigned to different hosts.

The invention claimed is:

1. A computer-implemented method for preprocessing test results for a plurality of tested biomarkers to provide reduced input data for subsequent input to a computer-based decision engine, said method comprising:

receiving, by a computing device, a patient's test results for a plurality of biomarkers, wherein the test result for each biomarker is at a first level of resolution, and further wherein the computing device includes a predefined data structure in which available biomarkers are associated with hosts, at least one host being associated with a plurality of biomarkers; and reducing the test results to input data by mapping the tested biomarkers to the predefined data structure, thereby identifying a set of hosts, and assigning a host value to each host in said set of hosts, wherein the host value is determined by the computing device based on the test results of the tested biomarker(s) mapped to the host, wherein said host value is provided at a second level of resolution;

thereby providing reduced input data indicative of the set of hosts and the assigned host values for each host in said set for subsequent input to a computer-based decision engine for generating clinical decision support.

2. The method of claim 1, wherein the structure comprises hosts in a hierarchy of levels.

3. The method of claim 1, wherein the number of hosts in the set of hosts is less than the number of available biomarkers.

4. The method of claim 1, wherein the second level of resolution is lower than the first level of resolution.

5. The method of claim 1, further comprising the step of scaling the test results or the host values based on patient-specific background data for the test results.

6. The method of claim 5, wherein the patient-specific background data comprises at least one of demographic data, anamnesis, heredity factors, response pattern, patient history and genetic data.

7. The method of claim 5, wherein said input data includes at least part of the patient-specific background data.

8. The method of claim 1, further comprising the step of receiving by the computing device at least one patient symptom, and wherein said input data includes data indicative of the patient symptom.

9. The method of claim 1, wherein the tested biomarkers are members of the Immunoglobulin super-family, and tested for in blood.

10. The method of claim 1, wherein the number of available biomarkers is about 10 or more.

11. The method of claim 1, wherein the tested biomarkers are antibodies.

12. The method of claim 1, wherein said clinical decision support is related to diagnosis of allergy or autoimmune diseases.

13. The method of claim 1, wherein said predefined data structure represents known relationships between said biomarkers and hosts.

14. A non-transitory computer-readable medium comprising instructions for causing a computer to perform the method of claim 1.

15. An electronic data processing system for enabling clinical decision support based on test results for a plurality of tested biomarkers, wherein each test result is provided at a first level of resolution, said system configured to receive a patient's test results for a plurality of biomarkers, said system comprising:

a computing device having at least one processor;

a predefined data structure in which available biomarkers are associated with hosts, at least one host being associated with a plurality of biomarkers;

a data reduction module for identifying a set of hosts by mapping the tested biomarkers to the data structure and for assigning a host value to each host in said set of hosts based on the test results of the tested biomarker(s) mapped to the host, wherein said host value is at a second level of resolution, thus providing input data identifying the set of hosts and the assigned host values for each host in said set suitable for input to a computer-based decision engine for generating clinical decision support.

16. The system of claim 15, further comprising a scaling module for scaling the test results or the host values based on patient-specific background data for the test results.

17. The system of claim 15, further comprising a computer-based decision engine for generating clinical decision support based on the input data provided by the data reduction module.

18. The system of claim 15, further comprising a component for generating the test results.

19. The system of claim 18, wherein said component for generating the test results comprises an analytical instrument specifically designed to test predefined subsets of biomarkers using an in vitro IgE ab detection technology.

20. The system of claim 15, wherein said computing device, data structure and data reduction module are integrated in a unitary device.

* * * * *